United States Patent
Ducray et al.

(10) Patent No.: US 8,338,490 B2
(45) Date of Patent: Dec. 25, 2012

(54) COMPOSITION FOR REPELLING AND DETERRING VERMIN

(75) Inventors: Pierre Ducray, Village-Neuf (FR); Tania Cavaliero, Neuchatel (CH); Maike Lohrmann, Birsfelden (CH); Jacques Bouvier, Neuchâtel (CH)

(73) Assignee: Novartis AG, Basel (CH)

( * ) Notice: Subject to any disclaimer, the term of this patent is extended or adjusted under 35 U.S.C. 154(b) by 446 days.

(21) Appl. No.: 12/515,663

(22) PCT Filed: Nov. 21, 2007

(86) PCT No.: PCT/EP2007/062619
§ 371 (c)(1), (2), (4) Date: May 20, 2009

(87) PCT Pub. No.: WO2008/062006
PCT Pub. Date: May 29, 2008

(65) Prior Publication Data
US 2010/0063090 A1    Mar. 11, 2010

(30) Foreign Application Priority Data
Nov. 24, 2006 (EP) .................................... 06124771

(51) Int. Cl.
*A01N 33/02* (2006.01)
*A61K 31/13* (2006.01)
*A61K 31/135* (2006.01)

(52) U.S. Cl. ........ 514/663; 514/667; 514/646; 514/647; 514/649

(58) Field of Classification Search .................. None
See application file for complete search history.

(56) References Cited

U.S. PATENT DOCUMENTS
2004/0067212 A1 * 4/2004 Tokuyama et al. ......... 424/70.21
2010/0093827 A1 * 4/2010 Yu et al. ...................... 514/423

FOREIGN PATENT DOCUMENTS
| EP | 0 281 908 | | 3/1988 |
| EP | 0 348 550 | | 1/1990 |
| EP | 1 692 939 A1 | | 8/2006 |
| WO | WO 9836733 | * | 8/1998 |
| WO | WO 99/65308 | | 12/1999 |

OTHER PUBLICATIONS

Zhao et al., "Syntheses of 1,2-Diamino and 1,2-Aminoalcohol Deivatives in the Piperidine and Pyrrolidine Series as Anti-amnesic Agents", Biorganic & Medicinal Chemistry 7, 1647-1654 (1999).

* cited by examiner

*Primary Examiner* — Alton Pryor
(74) *Attorney, Agent, or Firm* — Ann R. Pokalsky; Dilworth & Barrese, LLP

(57) ABSTRACT

The invention describes essentially a non-therapeutical process for deterring vermin, which is based on the usage of the largely known beta amino-alcohol derivatives of formula (I), as defined herein before. Furthermore, it describes the corresponding vermin-deterring compositions which contain these substances as the active ingredient, compounds of the formula (I) for the preparation of vermin-deterring compositions, and the use of compounds of formula (I) in the defense against vermin. Thus, the invention describes how and in which form the compounds of the formula (I) or their acid addition salts are used to deter vermin from materials, places or warm-blooded animals.

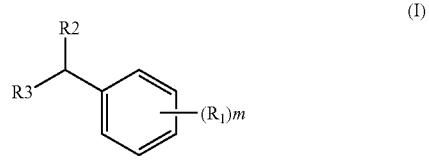

(I)

8 Claims, No Drawings

COMPOSITION FOR REPELLING AND DETERRING VERMIN

RELATED APPLICATION

This is a national stage application under 35 U.S.C. §371 of PCT International Application No. PCT/EP2007/062619, filed Nov. 21, 2007, which claims priority to European Application Number 06124771.4, filed Nov. 24, 2006, each of which is incorporated by reference in its entirety.

The present invention relates essentially to a non-therapeutical process for deterring vermin, which is based on the usage of the largely known beta amino-alcohol derivatives of formula I shown below. Furthermore, it relates to corresponding vermin-repelling compositions which contain these substances as the active ingredient, to compounds of formula I for the preparation of vermin-deterring compositions, and to the use of compounds of formula I in the defense against vermin.

It has surprisingly been found that the compounds of formula I below

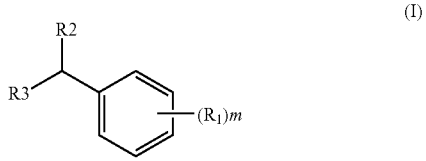

or their acid addition salts, wherein
R1 is hydrogen, halogen, $NH_2$, OH, $C_1$-$C_3$-alkyl or $C_1$-$C_3$-alkoxy;
m is 1, 2 or 3;
R2 is hydrogen, halogen, unsubstituted or substituted benzyl, —C(O)—R8, $C_1$-$C_{20}$-alkyl, halo-$C_1$-$C_{20}$-alkyl, $C_2$-$C_{20}$-alkenylalkyl, $C_3$-$C_6$-cycloalkyl, $C_1$-$C_{20}$-alkoxyalkyl, $C_1$-$C_{20}$-hydroxyalkyl, $C_1$-$C_{20}$-alkoxy, unsubstituted or substituted aryl
R3 is a substituent selected from the group consisting of

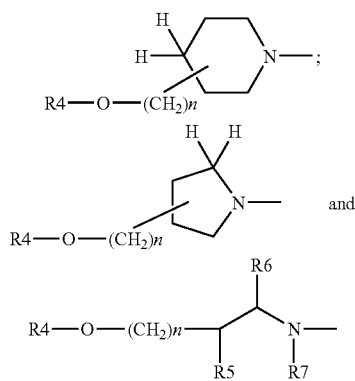

R4 is hydrogen, $C_1$-$C_{20}$-alkoxymethyl, benzyl, —C(O)—R8;
n is 0 or 1;
R5, R6 and R7 are each independently of each other hydrogen, halogen, unsubstituted or substituted benzyl, $C_1$-$C_{20}$-alkyl, halo-$C_1$-$C_{20}$-alkyl, $C_2$-$C_{20}$-alkenylalkyl, $C_3$-$C_6$-cycloalkyl, $C_1$-$C_{20}$-alkoxyalkyl, $C_1$-$C_{20}$-hydroxyalkyl, $C_1$-$C_{20}$-alkoxy, unsubstituted or substituted aryl; and
R8 is $C_1$-$C_{20}$-alkyl, $C_1$-$C_{20}$-alkoxy, unsubstituted or substituted aryl, unsubstituted or substituted aryloxy, benzyl, benzyloxy are eminently suitable for deterring vermin. Through the usage according to the invention of the above compounds, the most varied vermin of humans, animals, objects or certain places can be deterred, whereby numerous compounds within the scope of formula I are notable for their particularly long duration of efficacy.

Compounds of formula I having at least one basic centre may form e.g. acid addition salts. These are formed for example with strong inorganic acids, such as mineral acids, e.g. perchloric acid, sulphuric acid, nitric acid, nitrous acid, a phosphoric acid or a hydrohalic acid, with strong organic carboxylic acids, typically $C_1$-$C_4$alkanecarboxylic acids substituted where appropriate for example by halogen, e.g. acetic acid, such as dicarboxylic acids that are unsaturated where appropriate, e.g. oxalic, malonic, succinic, maleic, fumaric or phthalic acid, typically hydroxycarboxylic acids, e.g. ascorbic, lactic, malic, tartaric or citric acid, or benzoic acid, or with organic sulphonic acids, typically $C_1$-$C_4$alkanesulphonic or arylsulphonic acids substituted where appropriate for example by halogen, e.g. methanesulphonic or p-toluenesulphonic acid. Of the salts, particular preference is given to those formed with strong acids, especially with mineral acids, in particular with the hydrohalic acids HCl and HBr.

All multiple substitutions are to be interpreted such that identical or different substituents may occur simultaneously.

The alkyl groups present in the definitions of the substituents may be straight-chained or branched, depending on the number of carbon atoms, and they may be for example methyl, ethyl, propyl, butyl, pentyl, hexyl, heptyl, octyl, nonyl, decyl, undecyl, dodecyl, tetradecyl, hexadecyl, octadecyl, eicosyl, etc. as well as the branched isomers thereof, for example isopropyl, isobutyl, sec.-butyl, tert.-butyl, isopentyl, neopentyl or isohexyl. Alkoxy, haloalkyl and haloalkoxy radicals are derived from the said alkyl groups.

Halo or halogen normally signifies fluorine, chlorine, bromine or iodine, preferably fluorine or chlorine, especially fluorine, whereby the corresponding substituent or group may contain one or more identical or different halogen atoms.

Halogen-substituted carbon-containing groups, such as haloalkyl or haloalkoxy, may be partially halogenated or perhalogenated, whereby in the case of multiple halogenation, the halogen substituents may be identical or different. Examples of haloalkyl—as a group per se and as structural element of other groups and compounds such as haloalkoxy—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; and butyl or one of its isomers, mono- to nonasubstituted by fluorine, chlorine and/or bromine, such as $CF(CF_3)CHFCF_3$ or $CH_2(CF_2)_2CF_3$.

Alkenyl—as a group per se and as structural element of other groups and compounds such as alkeneoxy, halogenalkenyl or halogenalkeneoxy—is, in each case with due consideration of the specific number of carbon atoms in the group or compound in question, either straight-chained, for example vinyl, 1-methylvinyl, allyl, 1-butenyl or 2-hexenyl, or branched, for example isopropenyl.

Appropriate cycloalkyl substituents contain 3 to 8 carbon atoms and are, for example, cyclopropyl, cyclobutyl, cyclopentyl, cyclohexyl, cycloheptyl or cyclooctyl. Corresponding cycloalkenyl substituents may be mono- or also repeatedly unsaturated, for example cyclopentadienyl or cyclooctatetraenyl. Cyclopentyl and cyclohexyl are preferred.

In the context of the present invention, aryl is understood to be phenyl or naphthyl, especially phenyl. These aryl groups are either unsubstituted or are substituted once or up to three, in rare cases four times by $C_1$-$C_3$-alkyl, $C_1$-$C_3$-haloalkyl, $C_1$-$C_3$-alkoxy, $C_1$-$C_3$-haloalkoxy, halogen, cyano, hydroxyl, amino or nitro, whereby each multiple substitution is not limited to identical substituents; instead, mixed substituents may appear. Amongst the substituents $C_1$-$C_3$-alkyl, $C_1$-$C_3$-haloalkyl, $C_1$-$C_3$-alkoxy, $C_1$-$C_3$-haloalkoxy those with only one C-atom are most preferred.

Alkoxy groups preferably have a chain length of 1 to 6 carbon atoms. Even more preferred are alkoxy groups having a chain length of 1 to 3 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Haloalkoxy groups preferably have a chain length of 1 to 6 carbon atoms. Haloalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkoxyalkyl stands for an alkyl group wherein the chain of carbon atoms is preferably once interrupted by an oxygen atom. A hydroxyalkyl is an alkyl group carrying preferably one hydroxyl group.

Within the compounds of the formula I the following subgroups of compounds are especially preferred due to their pronounced repelling activity:

A compound of the formula Ia

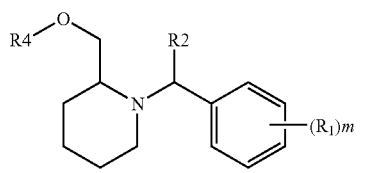

(Ia)

wherein R1, R2 and R4 have the meanings specified under formula I. Most preferred within the formula Ia are compounds wherein R1 is hydrogen; halogen, especially fluorine or chlorine; m is 1 or 2; R2 is hydrogen, $C_1$-$C_3$-alkyl, especially methyl; or phenyl; R4 is hydrogen or acetyl. Specific examples of representatives of the formula Ia are provided in table 1 hereinafter. Compounds of the formula Ia are commercially available, for example from Apollo Chemical Company, LLC; Burlington, N.C., USA.

A compound of the formula Ib

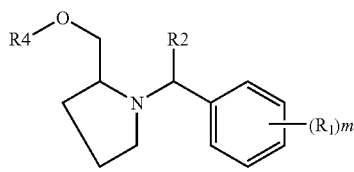

(Ib)

wherein R1, R2, R4 and m have the meanings specified under formula I. Most preferred within the formula Ib are compounds wherein R1 is hydrogen; halogen, especially fluorine or chlorine; m is 1 or 2; R2 is hydrogen, $C_1$-$C_3$-alkyl, especially methyl; or phenyl; R4 is hydrogen or acetyl. Specific examples of representatives of the formula Ib are provided in table 2 hereinafter. Compounds of the formula Ib are commercially available, for example from Sigma-Aldrich Chemie Gmbh, Munich, Germany or Fluka Chemie AG, Buchs, Switzerland or Chembridge, San Diego, Calif., USA or ABCR GmbH & Co. KG, Karlsruhe, Germany.

A compound of the formula Ic

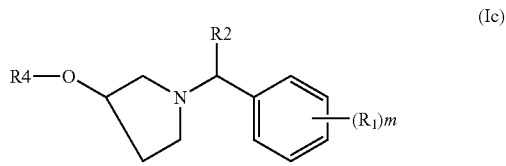

(Ic)

wherein R1, R2, R4 and m have the meanings specified under formula I. Most preferred within the formula Ib are compounds wherein R1 is hydrogen; halogen, especially fluorine or chlorine; m is 1 or 2; R2 is hydrogen, $C_1$-$C_3$-alkyl, especially methyl; or phenyl; R4 is hydrogen or acetyl. Specific examples of representatives of the formula Ic are provided in table 3 hereinafter. Compounds of the formula Ic are commercially available, for example from Sigma-Aldrich Chemie Gmbh, Munich, Germany or Fluka Chemie AG, Buchs, Switzerland or ABCR GmbH & Co. KG, Karlsruhe, Germany or Apollo Chemical Company, LLC; Burlington, N.C., USA or Beta Pharma, Inc., New Haven, Conn., USA or Oakwood Products, Inc., West Columbia, S.C. USA or TCI America, Portland, Oreg., USA.

A compound of the formula Id

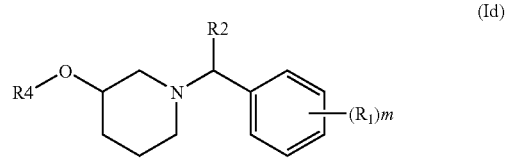

(Id)

wherein R1, R2, R4 and m have the meanings specified under formula I. Most preferred within the formula Id are compounds wherein R1 is hydrogen; halogen, especially fluorine or chlorine; m is 1 or 2; R2 is hydrogen, $C_1$-$C_3$-alkyl, especially methyl; or phenyl; R4 is hydrogen or acetyl. Specific examples of representatives of the formula Id are provided in table 4 hereinafter. Compounds of the formula Id are commercially available, for example from Sigma-Aldrich Chemie Gmbh, Munich, Germany or Fluka Chemie AG, Buchs, Switzerland or ABCR GmbH & Co. KG, Karlsruhe, Germany or Apollo Chemical Company, LLC; Burlington, N.C., USA or Beta Pharma, Inc., New Haven, Conn., USA or Acros Organics, Geel, Belgium or Alfa Chemicals Ltd., Binfield, Bracknell, Berkshire, UK or Alfa Aesar GmbH & Co KG, Karlsruhe, Germany.

A compound of the formula Ie

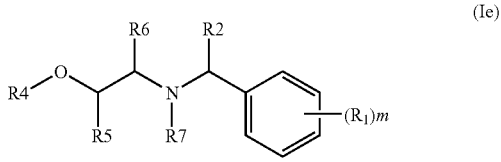

wherein R1, R2, R4 and m have the meanings specified under formula I. Most preferred within the formula Ie are compounds wherein R1 is hydrogen; halogen, especially fluorine or chlorine; m is 1 or 2; R2 is hydrogen, $C_1$-$C_3$-alkyl, especially methyl; or phenyl; R4 is hydrogen or acetyl; R5 is hydrogen, R6 is hydrogen or phenyl; and R7 is hydrogen, $C_1$-$C_3$-alkyl, especially methyl; or benzyl. Specific examples of representatives of the formula Ie are provided in table 5 hereinafter. Compounds of the formula Ie are commercially available, for example from Sigma-Aldrich Chemie Gmbh, Munich, Germany or ABCR GmbH & Co. KG, Karlsruhe, Germany or Alfa Chemicals Ltd., Binfield, Bracknell, Berkshire, UK or or TCI America, Portland, Oreg., USA or Bio-NEt, Newcastle University, NE2 4HH, UK.

Any of the compounds selected from the following group constitutes a most preferred embodiment of the present invention: Acetic acid 2-dibenzylamino-ethyl ester; Dibenzylamino-ethanol; 2-Propyl-pentanoic acid 2-dibenzylamino-ethyl ester; 1-Benzyl-pyrrolidin-3-ol; Acetic acid 1-benzyl-pyrrolidin-3-yl ester; 2,2-Dimethyl-propionic acid 1-benzyl-pyrrolidin-3-yl ester; Benzoic acid 1-benzyl-pyrrolidin-3-yl ester; (1-Benzyl-pyrrolidin-2-yl)-methanol; 1-Benzyl-piperidin-3-ol; (1-Benzyl-piperidin-2-yl)-methanol; 2-(Benzyl-methylamino)-ethanol; 2-Dibenzylamino-propan-1-ol; 2-Benzylamino-ethanol; and 2-Benzylamino-1-phenyl-ethanol.

The majority of the compounds of the present invention is commercially available or can be produced in the same way as the commercially available representatives. The compounds of the present invention can be produced by a variety of methods, for example, as shown in Scheme 1 below. Thus an amino-alcohol with a protected hydroxyl group may react with a benzylic carbon activated by a chlorine, bromine, iodine atom or alternatively by any other leaving groups such as tosylate, mesylate or triflate. This reaction may or not require the presence of a base (e.g. tertiary amines such as triethylamine, diisopropylethylamine), it can be carried out at a temperature of between 0° C. and 100° C. in an organic solvent such as THF, dichloromethane. The protective group can be removed using well known conditions (Protective Groups in Organic Synthesis, T. W. Greene/P. G. M. Wuts, Wiley Interscience).

Prodrugs (ester, alkyloxymethyl derivatives) of the free hydroxy molecule can be synthesized by reacting the hydroxyl group with alkyloxymethylchlorid to generate acetals or by classical esterification between the hydroxyl group and a carboxylic acid or its corresponding acid chloride.

SCHEME 1

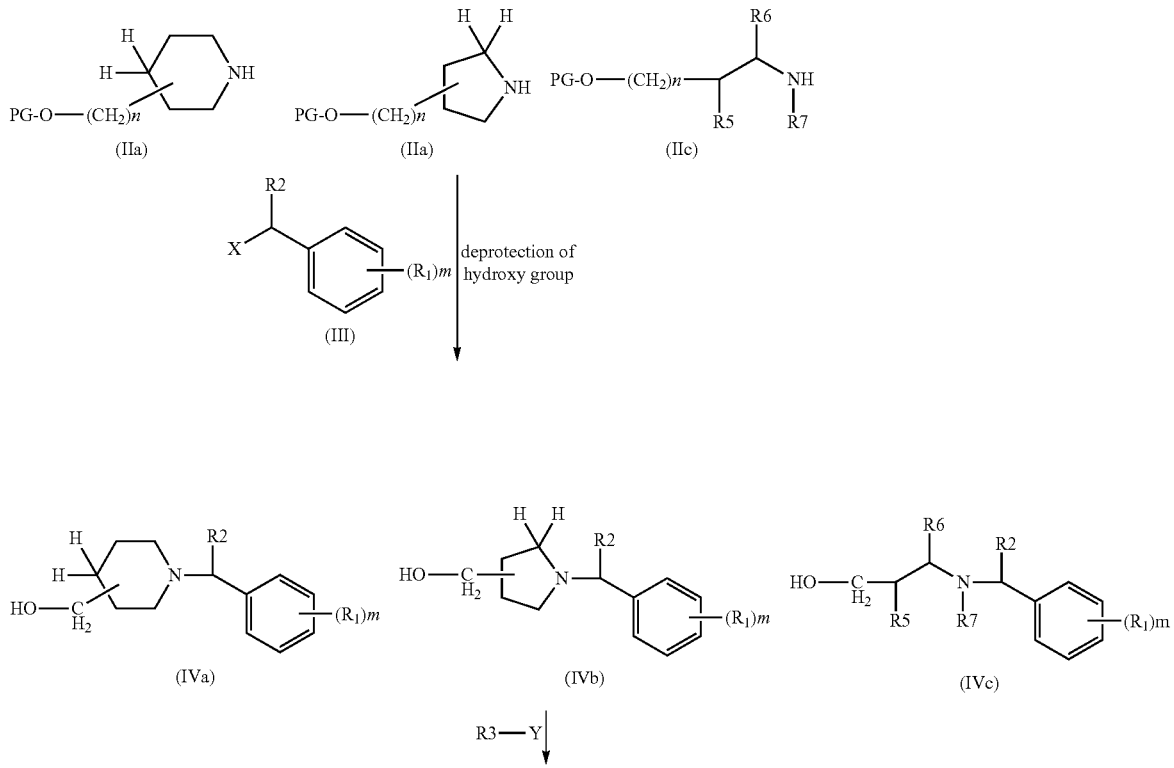

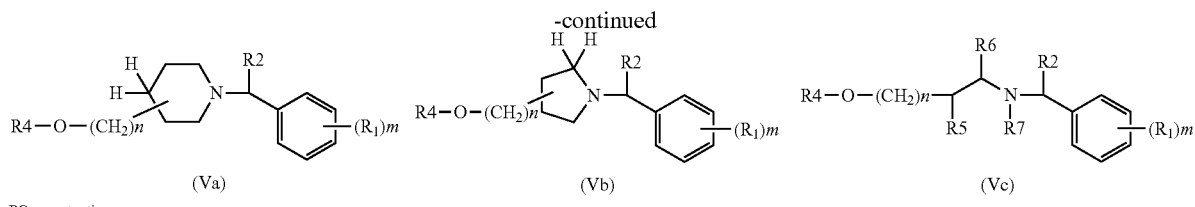

PG = protective group
X = leaving group
e.g. Cl, Br, I, tosylate, mesylate
Y = halogen, OH
R3 - C1-C20-alkyloxyalkyl, —C(O)—R4
R4 = akyl, aryl, etc ...

For the compounds of formula Id another syntheses may be used as described in Scheme 2. They enable quick access to unsubstituted or substituted beta aminoalcohol from the corresponding secondary amine. Benzylamines can react with ethylcarbonate to generate the corresponding unsubstituted amino alcohol without use of any solvent but presence of tetrabutylammonium iodide. The substituted amino alcohol are prepared by nucleophilic attack of nitrogen atom on hydroxyl-protected ethanol substituted by a leaving group X. The reaction is classically run in THF or similar organic solvent with a base (e.g. tertiary amines such as triethylamine, diisopropylethylamine).

As mentioned previously for scheme 1 prodrugs (ester, alkyloxymethyl derivatives) of the free hydroxy molecule can be synthesized by reacting the hydroxyl group with alkyloxymethylchlorid to generate acetals or by classical esterification between the hydroxyl group and a carboxylic acid or its corresponding acid chloride.

SCHEME 2

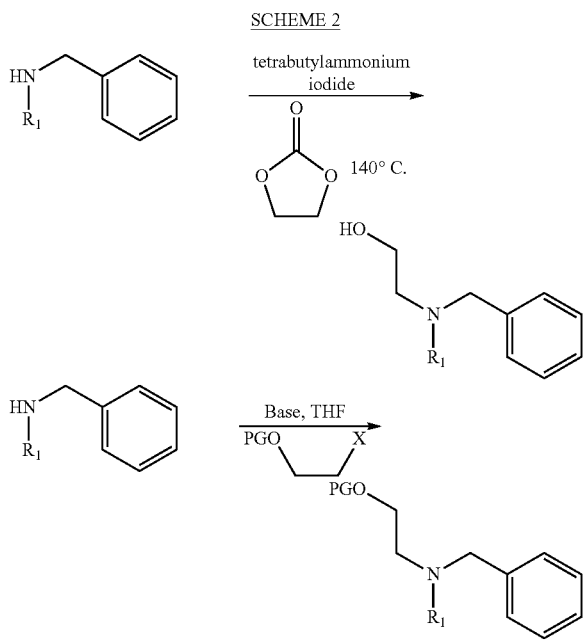

X = leaving group (e.g. Cl, Br, I, tosylate, mesylate)
PG = protective group

The compounds of formula I may be in the form of one of the possible isomers or in the form of a mixture thereof, for example depending upon the number of asymmetric carbon atoms and the absolute and relative configuration thereof, in the form of pure isomers or in the form of mixtures of isomers, such as mixtures of enantiomers or mixtures of diastereoisomers. The invention relates both to the pure isomers and to all possible mixtures of isomers and this is to be understood accordingly hereinbefore and hereinafter, even when stereochemical details are not specifically mentioned in each case.

Mixtures of diastereoisomers and mixtures of racemates of compounds of formula I obtainable in accordance with the process—depending upon the starting materials and procedures chosen—or by other means can be separated into the pure diastereoisomers or racemates in known manner on the basis of the physico-chemical differences between the constituents, for example by fractional crystallisation, distillation and/or chromatography. Mixtures of enantiomers or racemates so obtainable can be separated into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific immobilised enzymes, or via the formation of inclusion compounds, for example using chiral crown ethers, in which case only one enantiomer is complexed. Pure diastereoisomers and enantiomers can be obtained not only by separation of corresponding mixtures of isomers but also, according to the invention, by generally known methods of diastereoselective or enantioselective synthesis, for example by carrying out the process according to the invention with starting materials that have appropriate stereo-chemistry.

In the context of the present invention, vermin are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the vermin which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and midges (Nematocera), such as Culicidae, Simuliidae, Psychodidae, but also blood-sucking vermin, for example fleas, such as *Ctenocephalides fells* and *Ctenocephalides canis* (cat and dog fleas), *Xenopsylla cheopis, Pulex irritans, Dermatophilus penetrans*, lice, such as *Damalina ovis, Pediculus humanis*, biting flies and horseflies (Tabanidae), *Haematopota* spp. such as *Haematopota pluvialis, Tabanidea* spp. such as *Tabanus nigrovittatus, Chrysopsinae* spp. such as *Chrysops caecutiens*, tsetse flies, such as species of *Glossinia*, biting insects, particularly cockroaches, such as *Blatella germanica, Blatta orientalis*,

*Periplaneta americana*, mites, such as *Dermanyssus gallinae, Sarcoptes scabiei, Psoroptes ovis* and *Psorergates* spp. and last but not least ticks. The latter belong to the order Acarina. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

Ticks may be divided into hard and soft ticks, and are characterised by infesting one, two or three host animals. They attach themselves to a passing host animal and suck the blood or body fluids. Fully engorged female ticks drop from the host animal and lay large amounts of eggs (2000 to 3000) in a suitable crack in the floor or in any other protected site where the larvae hatch. These in turn seek a host animal, in order to suck blood from it. Larvae of ticks which only infest one host animal moult twice and thus become nymphs and finally adult ticks without leaving the host they have selected. Larvae of ticks which infest two or three host animals leave the animal after feeding on the blood, moult in the local environment and seek a second or third host as nymphs or as adult ticks, in order to suck its blood. Ticks are responsible world-wide for the transmission and spread of many human and animal diseases. Because of their economic influence, the most important ticks are *Boophilus, Rhipicephalus, Ixodes, Hyalomma, Amblyomma* and *Dermacentor*. They are carriers of bacterial, viral, rickettsial and protozoal diseases and cause tick-paralysis and tick-toxicosis. Even a single tick can cause paralysis whereby its saliva penetrates into the host animal during ingestion. Diseases caused by ticks are usually transmitted by ticks, which infest several host animals. Such diseases, for example babesiosis, anaplasmosis, theileriasis and heart water disease, are responsible for the death or impairment of a large number of domestic and farm animals in the entire world. In many countries of temperate climate, Ixodide ticks transmit the agent of the chronically harmful Lyme's disease from wild animals to humans. Apart from the transmission of disease, the ticks are responsible for great economic losses in livestock production. Losses are not confined to the death of the host animals, but also include damage to the pelts, loss of growth, a reduction in milk production and reduced value of the meat. Although the harmful effects of a tick infestation on animals have been known for years, and enormous progress has been made using tick-control programmes, until now no completely satisfactory methods of controlling or eliminating these parasites have been found, and in addition, ticks have often developed resistance to chemical active ingredients.

The infestation of fleas on domestic animals and pets likewise still represents for the owner a problem which has not been satisfactorily resolved or can only be resolved at considerable expense. As with ticks, fleas are not only troublesome, but are carriers of disease, and transmit various fungal diseases from host animal to host animal and to the animal keeper, particularly in moist, warm climatic areas, for example in the Mediterranean, in the southern part of USA, etc. Those at risk in particular are people with a weakened immune system or children whose immune system has not yet fully developed. Owing to their complex life cycle, none of the known methods for the control of fleas is completely satisfactory, especially as most known methods are basically directed towards the control of adult fleas in the pelt, and leave completely untouched the different juvenile stages of the fleas, which exist not only in the pelt of the animal, but also on the floor, in carpets, in the bedding of the animal, on chairs, in the garden and all other places with which the infested animal comes into contact. Flea treatment is usually expensive and has to be continued over long periods of time. Success usually depends on treating not only the infested animal, e.g. the dog or cat, but at the same time all the locations which the infested animal frequents.

Such a complicated procedure is unnecessary with the present compounds of formula (I), since a particular advantage of the compounds of formula I under discussion is that they are extremely effective and at the same time of very low toxicity both for the target parasites and for the warm-blooded animals. This is because their activity is based not on the death of the target parasite, but on the parrying defence thereof, before it attacks, sting, bites or in any other way harms the host organism. The presence of the compounds of formula I being discussed here appears to disturb the parasites in such a way that they suddenly leave the treated environment without biting or stinging, or even do not infest a treated host animal at all. What is striking is that the effect sets in when the parasite comes into contact with the active ingredient for a short time. After contact for a short time, the parasite avoids any further contact with the active ingredient. An additional advantage lies in the long-term action, e.g. compared with DEET (N,N-diethyl-m-toluamide), which although very effective, volatilizes rather rapidly and therefore has to be reapplied already after ca. 2 hours, and is thus not appropriate for the long-term treatment of animals. Usage of the present active ingredients is also pleasant because they are almost odorless.

Although the present active ingredients can of course be mixed with other substances having the same sphere of activity or with parasiticides or with other activity-improving substances to achieve further improved or longer-lasting action, and then applied, in contrast to many compounds of the prior art, this is totally unnecessary, as they already combine all the advantageous properties.

If the parasite is not only to be kept at bay, but also killed, of course this can be achieved by adding appropriate insecticides and/or acaricides. In practice, however, this is unnecessary in most cases.

The present active ingredients are preferably used in diluted form. Normally, they are brought to the final application form by using appropriate formulation excipients, and they then contain between 0.1 and 95% by weight, preferably 0.5 to 90% by weight of the active ingredient.

Since the active ingredients are in many instances applied to warm-blooded animals and of course come into contact with the skin, suitable formulation excipients are the excipients and administration forms that are known in cosmetics. They may be administered in the form of solutions, emulsions, ointments, creams, pastes, powders, sprays, etc.

For administration to farm animals or pets, such as cows, horses, asses, camels, dogs, cats, poultry, sheep, goats, etc., the so-called 'pour-on' or 'spot-on' formulations are especially suitable; these liquid or semi-liquid formulations have the advantage that they only have to be applied to a small area of the pelt or plumage, and, thanks to the proportion of spreading oils or other spreading additives, they disperse by themselves over the whole pelt or plumage, without having to do anything else, and become active over the whole area.

Of course, inanimate materials, for example clothing or dog and cat baskets, stables, carpets, curtains, living quarters, conservatories, etc. may be treated with said formulations and thus protected from parasite infestation.

To control cockroaches, their locus, usually cracks in the walls, furniture, etc., can be sprayed or powdered. Since cockroaches are extremely vigorous and it is almost impossible to drive them away completely, it is recommended that when using the present active ingredients, insecticides having activity against cockroaches are used additionally. For application on humans, a pleasant-smelling essence, e.g. a perfume, can be added to make application more attractive.

The following examples of preparation and usage of the active ingredients according to the invention serve to illustrate the invention without restricting it.

In particular, preferred formulations are made up as follows:

FORMULATION EXAMPLE 1

A vermin-deterring composition in the form of a lotion for application to the skin is prepared by mixing 30 parts of one of the active ingredients according to the invention selected from the compounds listed in one of the tables 1 to 5, 1.5 parts of perfume and 68.5 parts of isopropanol, whereby the latter may be replaced by ethanol.

FORMULATION EXAMPLE 2

A vermin-deterring composition in the form of an aerosol for spraying onto the pelt of a pet is prepared by formulating 50% active ingredient solution, consisting of 30 parts of one of the active ingredients according to the invention selected from the compounds listed in one of the tables 1 to 5, 1.5 parts of perfume and 68.5 parts of isopropanol, with 50% Frigen 11/12 (a halogenated hydrocarbon) as propellant gas in an aerosol can.

FORMULATION EXAMPLE 3

A vermin-deterring composition in the form of an aerosol for spraying onto the skin is prepared by formulating 40% active ingredient solution, consisting of 20 parts of one of the active ingredients according to the invention selected from the compounds listed in one of the tables 1 to 5, 1 part of perfume, 79 parts of isopropanol, with 60% propane/butane (in a ratio of 15:85) as propellant gas in an aerosol can.

PREPARATION EXAMPLE

Preparation Acetic acid 2-dibenzylamino-ethyl ester

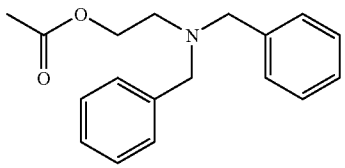

Step 1:

0.5 gram of dibenzylamine (2.5 mmol), 0.446 gram of ethylenecarbonate (5 mmol) and 0.215 gram of tetraethylammoniumiodide (083 mmol) were mixed together at room temperature. The solid mixture was then heated at 140° C. and the resulting suspension was stirred at this temperature for 26 hours. The reaction mixture was diluted with ethyl acetate and extracted with 10 mL of a 0.5M solution of sodium hydroxide. The aqueous phase was washed with ethyl acetate and the combined organic phases were washed twice with brine. The organic phase was dried on magnesium sulfate, filtered, concentrated under reduced pressure and purified by flash chromatography on silica gel (eluant: ethylacetate/hexane 1/2) to afford 0.5 gram of N,N-dibenzyl-2-aminoethanol (yield: 83%) as an oil.

Step 2:

18.5 grams (76.6 mmol) of N,N-dibenzyl-2-aminoethanol are diluted in dichloromethane (350 mL) at room temperature followed by the addition of N,N-diisopropylethylamine (16.47 mL, 99.7 mmol) and 4-dimethylaminopyridine (0.937 grams). The reaction is stirred for 15 minutes at 10° C. and 5.2 mL (92 mmol) of acetylchloride are added dropwise at 0° C. over 20 minutes. The reaction mixture is then stirred for 30 minutes at 0° C. and 20 hours at room temperature before the addition of 200 mL of a saturated aqueous solution of sodium bicarbonate. The organic phase is extracted, washed with brine, dried over magnesium sulfate, filtered and concentrated under reduced pressure to afford 23.48 grams of a yellowish oil. The oil is purified by flash chromatography on silica gel (eluant: ethylacetate/hexane 1/9) to afford 18.2 grams of title product as a colorless oil (83% yield).

The following tables exemplify compounds that can be used in accordance with the teaching of the present invention but do not limit it to theses specific examples.

TABLE 1

Non-limiting examples of compounds of the formula Ia (Ia)

| Compound No. | -(R1)m | R2 | R4 |
|---|---|---|---|
| 1.001 | H | H | H |
| 1.002 | 2-F | H | H |
| 1.003 | 3-F | H | H |
| 1.004 | 4-F | H | H |
| 1.005 | 2-Cl | H | H |
| 1.006 | 3-Cl | H | H |
| 1.007 | 4-Cl | H | H |
| 1.008 | 2,4-di-F | H | H |
| 1.009 | 3,4-di-F | H | H |
| 1.010 | 2,3-di-F | H | H |
| 1.011 | 2,5-di-F | H | H |
| 1.012 | 2,6-di-F | H | H |
| 1.013 | 3,5-di-F | H | H |
| 1.014 | H | Me | H |
| 1.015 | 2-F | Me | H |
| 1.016 | 3-F | Me | H |
| 1.017 | 4-F | Me | H |
| 1.018 | 2-Cl | Me | H |
| 1.019 | 3-Cl | Me | H |
| 1.020 | 4-Cl | Me | H |
| 1.021 | 2,4-di-F | Me | H |
| 1.022 | 3,4-di-F | Me | H |
| 1.023 | 2,3-di-F | Me | H |
| 1.024 | 2,5-di-F | Me | H |
| 1.025 | 2,6-di-F | Me | H |
| 1.026 | 3,5-di-F | Me | H |
| 1.027 | H | Phenyl | H |
| 1.028 | 2-F | Phenyl | H |
| 1.029 | 3-F | Phenyl | H |
| 1.030 | 4-F | Phenyl | H |
| 1.031 | 2-Cl | Phenyl | H |
| 1.032 | 3-Cl | Phenyl | H |
| 1.033 | 4-Cl | Phenyl | H |
| 1.034 | 2,4-di-F | Phenyl | H |

TABLE 1-continued

Non-limiting examples of compounds of the formula Ia

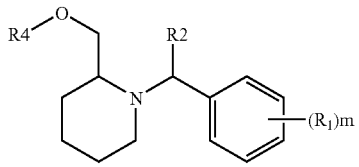

(Ia)

| Compound No. | -(R1)m | R2 | R4 |
|---|---|---|---|
| 1.035 | 3,4-di-F | Phenyl | H |
| 1.036 | 2,3-di-F | Phenyl | H |
| 1.037 | 2,5-di-F | Phenyl | H |
| 1.038 | 2,6-di-F | Phenyl | H |
| 1.039 | 3,5-di-F | Phenyl | H |
| 1.040 | H | H | Me-C(O)— |
| 1.041 | 2-F | H | Me-C(O)— |
| 1.042 | 3-F | H | Me-C(O)— |
| 1.043 | 4-F | H | Me-C(O)— |
| 1.044 | 2-Cl | H | Me-C(O)— |
| 1.045 | 3-Cl | H | Me-C(O)— |
| 1.046 | 4-Cl | H | Me-C(O)— |
| 1.047 | 2,4-di-F | H | Me-C(O)— |
| 1.048 | 3,4-di-F | H | Me-C(O)— |
| 1.049 | 2,3-di-F | H | Me-C(O)— |
| 1.050 | 2,5-di-F | H | Me-C(O)— |
| 1.051 | 2,6-di-F | H | Me-C(O)— |
| 1.052 | 3,5-di-F | H | Me-C(O)— |
| 1.053 | H | Me | Me-C(O)— |
| 1.054 | 2-F | Me | Me-C(O)— |
| 1.055 | 3-F | Me | Me-C(O)— |
| 1.056 | 4-F | Me | Me-C(O)— |
| 1.057 | 2-Cl | Me | Me-C(O)— |
| 1.058 | 3-Cl | Me | Me-C(O)— |
| 1.059 | 4-Cl | Me | Me-C(O)— |
| 1.060 | 2,4-di-F | Me | Me-C(O)— |
| 1.061 | 3,4-di-F | Me | Me-C(O)— |
| 1.062 | 2,3-di-F | Me | Me-C(O)— |
| 1.063 | 2,5-di-F | Me | Me-C(O)— |
| 1.064 | 2,6-di-F | Me | Me-C(O)— |
| 1.065 | 3,5-di-F | Me | Me-C(O)— |
| 1.066 | H | Phenyl | Me-C(O)— |
| 1.067 | 2-F | Phenyl | Me-C(O)— |
| 1.068 | 3-F | Phenyl | Me-C(O)— |
| 1.069 | 4-F | Phenyl | Me-C(O)— |
| 1.070 | 2-Cl | Phenyl | Me-C(O)— |
| 1.071 | 3-Cl | Phenyl | Me-C(O)— |
| 1.072 | 4-Cl | Phenyl | Me-C(O)— |
| 1.073 | 2,4-di-F | Phenyl | Me-C(O)— |
| 1.074 | 3,4-di-F | Phenyl | Me-C(O)— |
| 1.075 | 2,3-di-F | Phenyl | Me-C(O)— |
| 1.076 | 2,5-di-F | Phenyl | Me-C(O)— |
| 1.077 | 2,6-di-F | Phenyl | Me-C(O)— |
| 1.078 | 3,5-di-F | Phenyl | Me-C(O)— |

TABLE 2

Non-limiting examples of compounds of the formula Ib

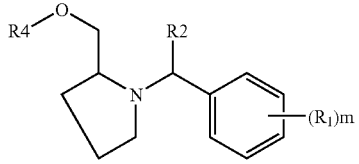

(Ib)

| Compound No. | -(R1)m | R2 | R4 |
|---|---|---|---|
| 2.001 | H | H | H |
| 2.002 | 2-F | H | H |
| 2.003 | 3-F | H | H |
| 2.004 | 4-F | H | H |
| 2.005 | 2-Cl | H | H |
| 2.006 | 3-Cl | H | H |
| 2.007 | 4-Cl | H | H |
| 2.008 | 2,4-di-F | H | H |
| 2.009 | 3,4-di-F | H | H |
| 2.010 | 2,3-di-F | H | H |
| 2.011 | 2,5-di-F | H | H |
| 2.012 | 2,6-di-F | H | H |
| 2.013 | 3,5-di-F | H | H |
| 2.014 | H | Me | H |
| 2.015 | 2-F | Me | H |
| 2.016 | 3-F | Me | H |
| 2.017 | 4-F | Me | H |
| 2.018 | 2-Cl | Me | H |
| 2.019 | 3-Cl | Me | H |
| 2.020 | 4-Cl | Me | H |
| 2.021 | 2,4-di-F | Me | H |
| 2.022 | 3,4-di-F | Me | H |
| 2.023 | 2,3-di-F | Me | H |
| 2.024 | 2,5-di-F | Me | H |
| 2.025 | 2,6-di-F | Me | H |
| 2.026 | 3,5-di-F | Me | H |
| 2.027 | H | Phenyl | H |
| 2.028 | 2-F | Phenyl | H |
| 2.029 | 3-F | Phenyl | H |
| 2.030 | 4-F | Phenyl | H |
| 2.031 | 2-Cl | Phenyl | H |
| 2.032 | 3-Cl | Phenyl | H |
| 2.033 | 4-Cl | Phenyl | H |
| 2.034 | 2,4-di-F | Phenyl | H |
| 2.035 | 3,4-di-F | Phenyl | H |
| 2.036 | 2,3-di-F | Phenyl | H |
| 2.037 | 2,5-di-F | Phenyl | H |
| 2.038 | 2,6-di-F | Phenyl | H |
| 2.039 | 3,5-di-F | Phenyl | H |
| 2.040 | H | H | Me-C(O)— |
| 2.041 | 2-F | H | Me-C(O)— |
| 2.042 | 3-F | H | Me-C(O)— |
| 2.043 | 4-F | H | Me-C(O)— |
| 2.044 | 2-Cl | H | Me-C(O)— |
| 2.045 | 3-Cl | H | Me-C(O)— |
| 2.046 | 4-Cl | H | Me-C(O)— |
| 2.047 | 2,4-di-F | H | Me-C(O)— |
| 2.048 | 3,4-di-F | H | Me-C(O)— |
| 2.049 | 2,3-di-F | H | Me-C(O)— |
| 2.050 | 2,5-di-F | H | Me-C(O)— |
| 2.051 | 2,6-di-F | H | Me-C(O)— |
| 2.052 | 3,5-di-F | H | Me-C(O)— |
| 2.053 | H | Me | Me-C(O)— |
| 2.054 | 2-F | Me | Me-C(O)— |
| 2.055 | 3-F | Me | Me-C(O)— |
| 2.056 | 4-F | Me | Me-C(O)— |
| 2.057 | 2-Cl | Me | Me-C(O)— |
| 2.058 | 3-Cl | Me | Me-C(O)— |
| 2.059 | 4-Cl | Me | Me-C(O)— |
| 2.060 | 2,4-di-F | Me | Me-C(O)— |
| 2.061 | 3,4-di-F | Me | Me-C(O)— |
| 2.062 | 2,3-di-F | Me | Me-C(O)— |
| 2.063 | 2,5-di-F | Me | Me-C(O)— |
| 2.064 | 2,6-di-F | Me | Me-C(O)— |
| 2.065 | 3,5-di-F | Me | Me-C(O)— |
| 2.066 | H | Phenyl | Me-C(O)— |
| 2.067 | 2-F | Phenyl | Me-C(O)— |
| 2.068 | 3-F | Phenyl | Me-C(O)— |
| 2.069 | 4-F | Phenyl | Me-C(O)— |

TABLE 2-continued

Non-limiting examples of compounds of the formula Ib (Ib)

| Compound No. | -(R1)m | R2 | R4 |
|---|---|---|---|
| 2.070 | 2-Cl | Phenyl | Me-C(O)— |
| 2.071 | 3-Cl | Phenyl | Me-C(O)— |
| 2.072 | 4-Cl | Phenyl | Me-C(O)— |
| 2.073 | 2,4-di-F | Phenyl | Me-C(O)— |
| 2.074 | 3,4-di-F | Phenyl | Me-C(O)— |
| 2.075 | 2,3-di-F | Phenyl | Me-C(O)— |
| 2.076 | 2,5-di-F | Phenyl | Me-C(O)— |
| 2.077 | 2,6-di-F | Phenyl | Me-C(O)— |
| 2.078 | 3,5-di-F | Phenyl | Me-C(O)— |

TABLE 3

Non-limiting examples of compounds of the formula Ic (Ic)

| Compound No. | -(R1)m | R2 | R4 |
|---|---|---|---|
| 3.001 | H | H | H |
| 3.002 | 2-F | H | H |
| 3.003 | 3-F | H | H |
| 3.004 | 4-F | H | H |
| 3.005 | 2-Cl | H | H |
| 3.006 | 3-Cl | H | H |
| 3.007 | 4-Cl | H | H |
| 3.008 | 2,4-di-F | H | H |
| 3.009 | 3,4-di-F | H | H |
| 3.010 | 2,3-di-F | H | H |
| 3.011 | 2,5-di-F | H | H |
| 3.012 | 2,6-di-F | H | H |
| 3.013 | 3,5-di-F | H | H |
| 3.014 | H | Me | H |
| 3.015 | 2-F | Me | H |
| 3.016 | 3-F | Me | H |
| 3.017 | 4-F | Me | H |
| 3.018 | 2-Cl | Me | H |
| 3.019 | 3-Cl | Me | H |
| 3.020 | 4-Cl | Me | H |
| 3.021 | 2,4-di-F | Me | H |
| 3.022 | 3,4-di-F | Me | H |
| 3.023 | 2,3-di-F | Me | H |
| 3.024 | 2,5-di-F | Me | H |
| 3.025 | 2,6-di-F | Me | H |
| 3.026 | 3,5-di-F | Me | H |
| 3.027 | H | Phenyl | H |
| 3.028 | 2-F | Phenyl | H |
| 3.029 | 3-F | Phenyl | H |
| 3.030 | 4-F | Phenyl | H |
| 3.031 | 2-Cl | Phenyl | H |
| 3.032 | 3-Cl | Phenyl | H |
| 3.033 | 4-Cl | Phenyl | H |
| 3.034 | 2,4-di-F | Phenyl | H |
| 3.035 | 3,4-di-F | Phenyl | H |
| 3.036 | 2,3-di-F | Phenyl | H |
| 3.037 | 2,5-di-F | Phenyl | H |
| 3.038 | 2,6-di-F | Phenyl | H |
| 3.039 | 3,5-di-F | Phenyl | H |
| 3.040 | H | H (Oil) | Me-C(O)— |
| 3.041 | 2-F | H | Me-C(O)— |
| 3.042 | 3-F | H | Me-C(O)— |
| 3.043 | 4-F | H | Me-C(O)— |
| 3.044 | 2-Cl | H | Me-C(O)— |
| 3.045 | 3-Cl | H | Me-C(O)— |
| 3.046 | 4-Cl | H | Me-C(O)— |
| 3.047 | 2,4-di-F | H | Me-C(O)— |
| 3.048 | 3,4-di-F | H | Me-C(O)— |
| 3.049 | 2,3-di-F | H | Me-C(O)— |
| 3.050 | 2,5-di-F | H | Me-C(O)— |
| 3.051 | 2,6-di-F | H | Me-C(O)— |
| 3.052 | 3,5-di-F | H | Me-C(O)— |
| 3.053 | H | Me | Me-C(O)— |
| 3.054 | 2-F | Me | Me-C(O)— |
| 3.055 | 3-F | Me | Me-C(O)— |
| 3.056 | 4-F | Me | Me-C(O)— |
| 3.057 | 2-Cl | Me | Me-C(O)— |
| 3.058 | 3-Cl | Me | Me-C(O)— |
| 3.059 | 4-Cl | Me | Me-C(O)— |
| 3.060 | 2,4-di-F | Me | Me-C(O)— |
| 3.061 | 3,4-di-F | Me | Me-C(O)— |
| 3.062 | 2,3-di-F | Me | Me-C(O)— |
| 3.063 | 2,5-di-F | Me | Me-C(O)— |
| 3.064 | 2,6-di-F | Me | Me-C(O)— |
| 3.065 | 3,5-di-F | Me | Me-C(O)— |
| 3.066 | H | Phenyl | Me-C(O)— |
| 3.067 | 2-F | Phenyl | Me-C(O)— |
| 3.068 | 3-F | Phenyl | Me-C(O)— |
| 3.069 | 4-F | Phenyl | Me-C(O)— |
| 3.070 | 2-Cl | Phenyl | Me-C(O)— |
| 3.071 | 3-Cl | Phenyl | Me-C(O)— |
| 3.072 | 4-Cl | Phenyl | Me-C(O)— |
| 3.073 | 2,4-di-F | Phenyl | Me-C(O)— |
| 3.074 | 3,4-di-F | Phenyl | Me-C(O)— |
| 3.075 | 2,3-di-F | Phenyl | Me-C(O)— |
| 3.076 | 2,5-di-F | Phenyl | Me-C(O)— |
| 3.077 | 2,6-di-F | Phenyl | Me-C(O)— |
| 3.078 | 3,5-di-F | Phenyl | Me-C(O)— |
| 3.079 | H | H (Oil) | Phe-C(O)— |
| 3.080 | H | H (Oil) | (CH$_3$)$_3$C—C(O)— |

TABLE 4

Non-limiting examples of compounds of the formula Id (Id)

| Compound No. | -(R1)m | R2 | R4 |
|---|---|---|---|
| 4.001 | H | H | H |
| 4.002 | 2-F | H | H |
| 4.003 | 3-F | H | H |
| 4.004 | 4-F | H | H |
| 4.005 | 2-Cl | H | H |
| 4.006 | 3-Cl | H | H |
| 4.007 | 4-Cl | H | H |
| 4.008 | 2,4-di-F | H | H |

TABLE 4-continued

Non-limiting examples of compounds of the formula Id (Id)

R4—O—[piperidine]—N—CH(R2)—[phenyl-(R1)m]

| Compound No. | -(R1)m | R2 | R4 |
|---|---|---|---|
| 4.009 | 3,4-di-F | H | H |
| 4.010 | 2,3-di-F | H | H |
| 4.011 | 2,5-di-F | H | H |
| 4.012 | 2,6-di-F | H | H |
| 4.013 | 3,5-di-F | H | H |
| 4.014 | H | Me | H |
| 4.015 | 2-F | Me | H |
| 4.016 | 3-F | Me | H |
| 4.017 | 4-F | Me | H |
| 4.018 | 2-Cl | Me | H |
| 4.019 | 3-Cl | Me | H |
| 4.020 | 4-Cl | Me | H |
| 4.021 | 2,4-di-F | Me | H |
| 4.022 | 3,4-di-F | Me | H |
| 4.023 | 2,3-di-F | Me | H |
| 4.024 | 2,5-di-F | Me | H |
| 4.025 | 2,6-di-F | Me | H |
| 4.026 | 3,5-di-F | Me | H |
| 4.027 | H | Phenyl | H |
| 4.028 | 2-F | Phenyl | H |
| 4.029 | 3-F | Phenyl | H |
| 4.030 | 4-F | Phenyl | H |
| 4.031 | 2-Cl | Phenyl | H |
| 4.032 | 3-Cl | Phenyl | H |
| 4.033 | 4-Cl | Phenyl | H |
| 4.034 | 2,4-di-F | Phenyl | H |
| 4.035 | 3,4-di-F | Phenyl | H |
| 4.036 | 2,3-di-F | Phenyl | H |
| 4.037 | 2,5-di-F | Phenyl | H |
| 4.038 | 2,6-di-F | Phenyl | H |
| 4.039 | 3,5-di-F | Phenyl | H |
| 4.040 | H | H | Me-C(O)— |
| 4.041 | 2-F | H | Me-C(O)— |
| 4.042 | 3-F | H | Me-C(O)— |
| 4.043 | 4-F | H | Me-C(O)— |
| 4.044 | 2-Cl | H | Me-C(O)— |
| 4.045 | 3-Cl | H | Me-C(O)— |
| 4.046 | 4-Cl | H | Me-C(O)— |
| 4.047 | 2,4-di-F | H | Me-C(O)— |
| 4.048 | 3,4-di-F | H | Me-C(O)— |
| 4.049 | 2,3-di-F | H | Me-C(O)— |
| 4.050 | 2,5-di-F | H | Me-C(O)— |
| 4.051 | 2,6-di-F | H | Me-C(O)— |
| 4.052 | 3,5-di-F | H | Me-C(O)— |
| 4.053 | H | Me | Me-C(O)— |
| 4.054 | 2-F | Me | Me-C(O)— |
| 4.055 | 3-F | Me | Me-C(O)— |
| 4.056 | 4-F | Me | Me-C(O)— |
| 4.057 | 2-Cl | Me | Me-C(O)— |
| 4.058 | 3-Cl | Me | Me-C(O)— |
| 4.059 | 4-Cl | Me | Me-C(O)— |
| 4.060 | 2,4-di-F | Me | Me-C(O)— |
| 4.061 | 3,4-di-F | Me | Me-C(O)— |
| 4.062 | 2,3-di-F | Me | Me-C(O)— |
| 4.063 | 2,5-di-F | Me | Me-C(O)— |
| 4.064 | 2,6-di-F | Me | Me-C(O)— |
| 4.065 | 3,5-di-F | Me | Me-C(O)— |
| 4.066 | H | Phenyl | Me-C(O)— |
| 4.067 | 2-F | Phenyl | Me-C(O)— |
| 4.068 | 3-F | Phenyl | Me-C(O)— |
| 4.069 | 4-F | Phenyl | Me-C(O)— |
| 4.070 | 2-Cl | Phenyl | Me-C(O)— |
| 4.071 | 3-Cl | Phenyl | Me-C(O)— |
| 4.072 | 4-Cl | Phenyl | Me-C(O)— |
| 4.073 | 2,4-di-F | Phenyl | Me-C(O)— |
| 4.074 | 3,4-di-F | Phenyl | Me-C(O)— |
| 4.075 | 2,3-di-F | Phenyl | Me-C(O)— |
| 4.076 | 2,5-di-F | Phenyl | Me-C(O)— |
| 4.077 | 2,6-di-F | Phenyl | Me-C(O)— |
| 4.078 | 3,5-di-F | Phenyl | Me-C(O)— |

TABLE 5

Non-limiting examples of compounds of the formula Ie (Ie)

R4—O—CH(R5)—CH(R6)—N(R7)—CH(R2)—[phenyl-(R1)m]

| No. | -(R1)m | R2 | R4 | R5 | R6 | R7 |
|---|---|---|---|---|---|---|
| 5.001 | H | H | H | H | H | Benzyl |
| 5.002 | 2-F | H | H | H | H | Benzyl |
| 5.003 | 3-F | H | H | H | H | Benzyl |
| 5.004 | 4-F | H | H | H | H | Benzyl |
| 5.005 | 2-Cl | H | H | H | H | Benzyl |
| 5.006 | 3-Cl | H | H | H | H | Benzyl |
| 5.007 | 4-Cl | H | H | H | H | Benzyl |
| 5.008 | 2,4-di-F | H | H | H | H | Benzyl |
| 5.009 | 3,4-di-F | H | H | H | H | Benzyl |
| 5.010 | 2,3-di-F | H | H | H | H | Benzyl |
| 5.011 | 2,5-di-F | H | H | H | H | Benzyl |
| 5.012 | 2,6-di-F | H | H | H | H | Benzyl |
| 5.013 | 3,5-di-F | H | H | H | H | Benzyl |
| 5.014 | H | Me | H | H | H | Benzyl |

TABLE 5-continued

Non-limiting examples of compounds of the formula Ie (Ie)

| No. | -(R1)m | R2 | R4 | R5 | R6 | R7 |
|---|---|---|---|---|---|---|
| 5.015 | 2-F | Me | H | H | H | Benzyl |
| 5.016 | 3-F | Me | H | H | H | Benzyl |
| 5.017 | 4-F | Me | H | H | H | Benzyl |
| 5.018 | 2-Cl | Me | H | H | H | Benzyl |
| 5.019 | 3-Cl | Me | H | H | H | Benzyl |
| 5.020 | 4-Cl | Me | H | H | H | Benzyl |
| 5.021 | 2,4-di-F | Me | H | H | H | Benzyl |
| 5.022 | 3,4-di-F | Me | H | H | H | Benzyl |
| 5.023 | 2,3-di-F | Me | H | H | H | Benzyl |
| 5.024 | 2,5-di-F | Me | H | H | H | Benzyl |
| 5.025 | 2,6-di-F | Me | H | H | H | Benzyl |
| 5.026 | 3,5-di-F | Me | H | H | H | Benzyl |
| 5.027 | H | Phenyl | H | H | H | Benzyl |
| 5.028 | 2-F | Phenyl | H | H | H | Benzyl |
| 5.029 | 3-F | Phenyl | H | H | H | Benzyl |
| 5.030 | 4-F | Phenyl | H | H | H | Benzyl |
| 5.031 | 2-Cl | Phenyl | H | H | H | Benzyl |
| 5.032 | 3-Cl | Phenyl | H | H | H | Benzyl |
| 5.033 | 4-Cl | Phenyl | H | H | H | Benzyl |
| 5.034 | 2,4-di-F | Phenyl | H | H | H | Benzyl |
| 5.035 | 3,4-di-F | Phenyl | H | H | H | Benzyl |
| 5.036 | 2,3-di-F | Phenyl | H | H | H | Benzyl |
| 5.037 | 2,5-di-F | Phenyl | H | H | H | Benzyl |
| 5.038 | 2,6-di-F | Phenyl | H | H | H | Benzyl |
| 5.039 | 3,5-di-F | Phenyl | H | H | H | Benzyl |
| 5.040 | H | H | Me-C(O)— | H | H | Benzyl (Oil) |
| 5.041 | 2-F | H | Me-C(O)— | H | H | Benzyl |
| 5.042 | 3-F | H | Me-C(O)— | H | H | Benzyl |
| 5.043 | 4-F | H | Me-C(O)— | H | H | Benzyl |
| 5.044 | 2-Cl | H | Me-C(O)— | H | H | Benzyl |
| 5.045 | 3-Cl | H | Me-C(O)— | H | H | Benzyl |
| 5.046 | 4-Cl | H | Me-C(O)— | H | H | Benzyl |
| 5.047 | 2,4-di-F | H | Me-C(O)— | H | H | Benzyl |
| 5.048 | 3,4-di-F | H | Me-C(O)— | H | H | Benzyl |
| 5.049 | 2,3-di-F | H | Me-C(O)— | H | H | Benzyl |
| 5.050 | 2,5-di-F | H | Me-C(O)— | H | H | Benzyl |
| 5.051 | 2,6-di-F | H | Me-C(O)— | H | H | Benzyl |
| 5.052 | 3,5-di-F | H | Me-C(O)— | H | H | Benzyl |
| 5.053 | H | Me | Me-C(O)— | H | H | Benzyl |
| 5.054 | 2-F | Me | Me-C(O)— | H | H | Benzyl |
| 5.055 | 3-F | Me | Me-C(O)— | H | H | Benzyl |
| 5.056 | 4-F | Me | Me-C(O)— | H | H | Benzyl |
| 5.057 | 2-Cl | Me | Me-C(O)— | H | H | Benzyl |
| 5.058 | 3-Cl | Me | Me-C(O)— | H | H | Benzyl |
| 5.059 | 4-Cl | Me | Me-C(O)— | H | H | Benzyl |
| 5.060 | 2,4-di-F | Me | Me-C(O)— | H | H | Benzyl |
| 5.061 | 3,4-di-F | Me | Me-C(O)— | H | H | Benzyl |
| 5.062 | 2,3-di-F | Me | Me-C(O)— | H | H | Benzyl |
| 5.063 | 2,5-di-F | Me | Me-C(O)— | H | H | Benzyl |
| 5.064 | 2,6-di-F | Me | Me-C(O)— | H | H | Benzyl |
| 5.065 | 3,5-di-F | Me | Me-C(O)— | H | H | Benzyl |
| 5.066 | H | Phenyl | Me-C(O)— | H | H | Benzyl |
| 5.067 | 2-F | Phenyl | Me-C(O)— | H | H | Benzyl |
| 5.068 | 3-F | Phenyl | Me-C(O)— | H | H | Benzyl |
| 5.069 | 4-F | Phenyl | Me-C(O)— | H | H | Benzyl |
| 5.070 | 2-Cl | Phenyl | Me-C(O)— | H | H | Benzyl |
| 5.071 | 3-Cl | Phenyl | Me-C(O)— | H | H | Benzyl |
| 5.072 | 4-Cl | Phenyl | Me-C(O)— | H | H | Benzyl |
| 5.073 | 2,4-di-F | Phenyl | Me-C(O)— | H | H | Benzyl |
| 5.074 | 3,4-di-F | Phenyl | Me-C(O)— | H | H | Benzyl |
| 5.075 | 2,3-di-F | Phenyl | Me-C(O)— | H | H | Benzyl |
| 5.076 | 2,5-di-F | Phenyl | Me-C(O)— | H | H | Benzyl |
| 5.077 | 2,6-di-F | Phenyl | Me-C(O)— | H | H | Benzyl |
| 5.078 | 3,5-di-F | Phenyl | Me-C(O)— | H | H | Benzyl |
| 5.079 | H | H | H | H | Phenyl | H |
| 5.080 | 2-F | H | H | H | Phenyl | H |
| 5.081 | 3-F | H | H | H | Phenyl | H |

TABLE 5-continued

Non-limiting examples of compounds of the formula Ie (Ie)

| No. | -(R1)m | R2 | R4 | R5 | R6 | R7 |
|---|---|---|---|---|---|---|
| 5.082 | 4-F | H | H | H | Phenyl | H |
| 5.083 | 2-Cl | H | H | H | Phenyl | H |
| 5.084 | 3-Cl | H | H | H | Phenyl | H |
| 5.085 | 4-Cl | H | H | H | Phenyl | H |
| 5.086 | 2,4-di-F | H | H | H | Phenyl | H |
| 5.087 | 3,4-di-F | H | H | H | Phenyl | H |
| 5.088 | 2,3-di-F | H | H | H | Phenyl | H |
| 5.089 | 2,5-di-F | H | H | H | Phenyl | H |
| 5.090 | 2,6-di-F | H | H | H | Phenyl | H |
| 5.091 | 3,5-di-F | H | H | H | Phenyl | H |
| 5.092 | H | Me | H | H | Phenyl | H |
| 5.093 | 2-F | Me | H | H | Phenyl | H |
| 5.094 | 3-F | Me | H | H | Phenyl | H |
| 5.095 | 4-F | Me | H | H | Phenyl | H |
| 5.096 | 2-Cl | Me | H | H | Phenyl | H |
| 5.097 | 3-Cl | Me | H | H | Phenyl | H |
| 5.098 | 4-Cl | Me | H | H | Phenyl | H |
| 5.099 | 2,4-di-F | Me | H | H | Phenyl | H |
| 5.100 | 3,4-di-F | Me | H | H | Phenyl | H |
| 5.101 | 2,3-di-F | Me | H | H | Phenyl | H |
| 5.102 | 2,5-di-F | Me | H | H | Phenyl | H |
| 5.103 | 2,6-di-F | Me | H | H | Phenyl | H |
| 5.104 | 3,5-di-F | Me | H | H | Phenyl | H |
| 5.105 | H | Phenyl | H | H | Phenyl | H |
| 5.106 | 2-F | Phenyl | H | H | Phenyl | H |
| 5.107 | 3-F | Phenyl | H | H | Phenyl | H |
| 5.108 | 4-F | Phenyl | H | H | Phenyl | H |
| 5.109 | 2-Cl | Phenyl | H | H | Phenyl | H |
| 5.110 | 3-Cl | Phenyl | H | H | Phenyl | H |
| 5.111 | 4-Cl | Phenyl | H | H | Phenyl | H |
| 5.112 | 2,4-di-F | Phenyl | H | H | Phenyl | H |
| 5.113 | 3,4-di-F | Phenyl | H | H | Phenyl | H |
| 5.114 | 2,3-di-F | Phenyl | H | H | Phenyl | H |
| 5.115 | 2,5-di-F | Phenyl | H | H | Phenyl | H |
| 5.116 | 2,6-di-F | Phenyl | H | H | Phenyl | H |
| 5.117 | 3,5-di-F | Phenyl | H | H | Phenyl | H |
| 5.118 | H | H | Me-C(O)— | H | Phenyl | H |
| 5.119 | 2-F | H | Me-C(O)— | H | Phenyl | H |
| 5.120 | 3-F | H | Me-C(O)— | H | Phenyl | H |
| 5.121 | 4-F | H | Me-C(O)— | H | Phenyl | H |
| 5.122 | 2-Cl | H | Me-C(O)— | H | Phenyl | H |
| 5.123 | 3-Cl | H | Me-C(O)— | H | Phenyl | H |
| 5.124 | 4-Cl | H | Me-C(O)— | H | Phenyl | H |
| 5.125 | 2,4-di-F | H | Me-C(O)— | H | Phenyl | H |
| 5.126 | 3,4-di-F | H | Me-C(O)— | H | Phenyl | H |
| 5.127 | 2,3-di-F | H | Me-C(O)— | H | Phenyl | H |
| 5.128 | 2,5-di-F | H | Me-C(O)— | H | Phenyl | H |
| 5.129 | 2,6-di-F | H | Me-C(O)— | H | Phenyl | H |
| 5.130 | 3,5-di-F | H | Me-C(O)— | H | Phenyl | H |
| 5.131 | H | Me | Me-C(O)— | H | Phenyl | H |
| 5.132 | 2-F | Me | Me-C(O)— | H | Phenyl | H |
| 5.133 | 3-F | Me | Me-C(O)— | H | Phenyl | H |
| 5.134 | 4-F | Me | Me-C(O)— | H | Phenyl | H |
| 5.135 | 2-Cl | Me | Me-C(O)— | H | Phenyl | H |
| 5.136 | 3-Cl | Me | Me-C(O)— | H | Phenyl | H |
| 5.137 | 4-Cl | Me | Me-C(O)— | H | Phenyl | H |
| 5.138 | 2,4-di-F | Me | Me-C(O)— | H | Phenyl | H |
| 5.139 | 3,4-di-F | Me | Me-C(O)— | H | Phenyl | H |
| 5.140 | 2,3-di-F | Me | Me-C(O)— | H | Phenyl | H |
| 5.141 | 2,5-di-F | Me | Me-C(O)— | H | Phenyl | H |
| 5.142 | 2,6-di-F | Me | Me-C(O)— | H | Phenyl | H |
| 5.143 | 3,5-di-F | Me | Me-C(O)— | H | Phenyl | H |
| 5.144 | H | Phenyl | Me-C(O)— | H | Phenyl | H |
| 5.145 | 2-F | Phenyl | Me-C(O)— | H | Phenyl | H |
| 5.146 | 3-F | Phenyl | Me-C(O)— | H | Phenyl | H |
| 5.147 | 4-F | Phenyl | Me-C(O)— | H | Phenyl | H |
| 5.148 | 2-Cl | Phenyl | Me-C(O)— | H | Phenyl | H |

TABLE 5-continued

Non-limiting examples of compounds of the formula Ie (Ie)

R4—O—C(R5)(R6)—C(R2)(H)—N(R7)—CH2—C6H4—(R1)m

| No. | -(R1)m | R2 | R4 | R5 | R6 | R7 |
|---|---|---|---|---|---|---|
| 5.149 | 3-Cl | Phenyl | Me-C(O)— | H | Phenyl | H |
| 5.150 | 4-Cl | Phenyl | Me-C(O)— | H | Phenyl | H |
| 5.151 | 2,4-di-F | Phenyl | Me-C(O)— | H | Phenyl | H |
| 5.152 | 3,4-di-F | Phenyl | Me-C(O)— | H | Phenyl | H |
| 5.153 | 2,3-di-F | Phenyl | Me-C(O)— | H | Phenyl | H |
| 5.154 | 2,5-di-F | Phenyl | Me-C(O)— | H | Phenyl | H |
| 5.155 | 2,6-di-F | Phenyl | Me-C(O)— | H | Phenyl | H |
| 5.156 | 3,5-di-F | Phenyl | Me-C(O)— | H | Phenyl | H |
| 5.157 | H | H | H | H | H | Me |
| 5.158 | 2-F | H | H | H | H | Me |
| 5.159 | 3-F | H | H | H | H | Me |
| 5.160 | 4-F | H | H | H | H | Me |
| 5.161 | 2-Cl | H | H | H | H | Me |
| 5.162 | 3-Cl | H | H | H | H | Me |
| 5.163 | 4-Cl | H | H | H | H | Me |
| 5.164 | 2,4-di-F | H | H | H | H | Me |
| 5.165 | 3,4-di-F | H | H | H | H | Me |
| 5.166 | 2,3-di-F | H | H | H | H | Me |
| 5.167 | 2,5-di-F | H | H | H | H | Me |
| 5.168 | 2,6-di-F | H | H | H | H | Me |
| 5.169 | 3,5-di-F | H | H | H | H | Me |
| 5.170 | H | H | Me-C(O)— | H | H | Me |
| 5.171 | 2-F | H | Me-C(O)— | H | H | Me |
| 5.172 | 3-F | H | Me-C(O)— | H | H | Me |
| 5.173 | 4-F | H | Me-C(O)— | H | H | Me |
| 5.174 | 2-Cl | H | Me-C(O)— | H | H | Me |
| 5.175 | 3-Cl | H | Me-C(O)— | H | H | Me |
| 5.176 | 4-Cl | H | Me-C(O)— | H | H | Me |
| 5.177 | 2,4-di-F | H | Me-C(O)— | H | H | Me |
| 5.178 | 3,4-di-F | H | Me-C(O)— | H | H | Me |
| 5.179 | 2,3-di-F | H | Me-C(O)— | H | H | Me |
| 5.180 | 2,5-di-F | H | Me-C(O)— | H | H | Me |
| 5.181 | 2,6-di-F | H | Me-C(O)— | H | H | Me |
| 5.182 | 3,5-di-F | H | Me-C(O)— | H | H | Me |
| 5.183 | H | H | (CH$_3$—CH$_2$—CH$_2$)$_2$CH—C(O)— | H | H | Benzyl (Oil) |
| 5.184 | H | H | H | H | Me | Benzyl |

BIOLOGICAL EXAMPLES

Arena Test: General Method for Testing Vermin-Deterring Substances

This method is carried out in titre plates having 6 wells with a cross-section of 5 cm each, using a computer-supported video system. Each well of the titre plate is lined with a circular filter paper or another suitable carrier material. The substance of formula I to be tested is dissolved in methanol, acetonitrile or another suitable solvent, with ultrasound treatment and heating being employed for poorly-soluble substances. In an amount of 1 to 100 µg/cm$^2$, the dissolved test substance is placed in the centre of the filter paper on a quadrant or circular area of ca. 2.4 cm$^2$ radius. 4 of the 6 wells are filled with different test substances or with the same test substance in different dilutions (e.g. 1, 3.2, 5, 10 and 20 µg/cm$^2$). The 5th well is treated with DEET (N,N-diethyl-m-toluamide) as standard substance. The 6th well is filled with the pure solvent and serves as a control. 60 to 100 larvae or 25 to 50 nymphs or 10 to 25 adults of the parasite to be tested, e.g. ticks, are added to each filter paper, and the system is covered with a pane of glass and positioned under a video camera.

At intervals of 5 seconds, the video camera takes individual pictures of all 6 wells. For a qualitative evaluation, these images are observed in a time-lapse as a continuous film, optically following the movements of the parasites on the filter paper and comparing them with the movements in the control well no. 6 or with the standard in the 5th well. A qualitative observation is thus made as to whether the test parasites move evenly over the whole surface of the filter paper and ignore the test substance, or whether and over what period they avoid the treated zone, and what influence the dilution of the test substance has on the behaviour of the test parasites. In this way, neutral and deterring substances are determined. At the same time, the duration of activity of the test substance is determined and compared with that of the standard. By plotting all the images for each individual well over one another, different areas of density are obtained. This represents the frequency at which the parasites visit certain places. This frequency is evaluated statistically and thus quantitatively by the Willcoxon method in a comparison with the control and with the standard. Compounds of Tables 1, 2, 3, 4, and 5 are tested according to this protocol with various parasites, for example the compounds Nos. 1.001, 2.001, 3.001, 4.001, 5.001, 5.184, 5.185, and 5.186 display excellent activity.

Arena Test In Vitro Against *Amblyomma hebraeum* or *variegatum* (nymphs)

The test is carried out as described above, with ca. 25 to 50 nymphs being added per well. 10 mg of dissolved test substance is applied to an area of 2.4 cm² radius. An evaluation of the video images shows that the compounds of formula I display marked deterrent action against *Amblyomma* nymphs, which lasts considerably longer than that of DEET. Particularly marked long-term activity is shown for example by using the compounds Nos. 1.001, 2.001, 3.001, 4.001, 5.001, 5.184, 5.185, and 5.186 even up to a dilution of 3.2 μg/cm².

Arena Test In Vitro Against *Boophilus microplus* Biarra (larvae)

The test is carried out as described above, with ca. 60 to 100 larvae being added per well. 10 mg of dissolved test substance is applied to an area of 2.4 cm² radius. An evaluation of the video images shows that the compounds of formula I display marked deterring action against *Boophilus* larvae, which lasts considerably longer than that of DEET. Particularly marked long-term activity is shown for example by using the compounds Nos. 1.001, 2.001, 3.001, 4.001, 5.001, 5.184, 5.185, and 5.186 even up to a dilution of 10 μg/cm².

Arena Test In Vitro Against *Rhipicephalus sanguineus* (nymphs)

A test is carried out analogously to example B using ca. 40 to 50 nymphs. An evaluation of the video images shows that the compounds according to the invention display good deterring action. In particular, the compounds are notable for their almost complete deterring action, which lasts considerably longer than that of DEET. Particularly marked long-term activity is shown for example by compounds Nos. 1.001, 2.001, 3.001, 4.001, 5.001, 5.184, 5.185, and 5.186 even up to a dilution of 10 μg/cm².

Analogous tests indicate a long term activity for various species of fly, such as *Musca domestica*.

What is claimed is:

1. A process for deterring vermin from warm-blooded animals other than human, said process comprising: applying topically, together with a spreading additive, to the skin, the pelt or the plumage of a warm-blooded animal other than human in need of defense against vermin, a compound of formula I

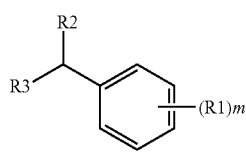

(I)

or their acid addition salts, wherein

R1 is hydrogen, halogen, $NH_2$, OH, $C_1$-$C_3$-alkyl or $C_1$-$C_3$-alkoxy;

m is 1, 2 or 3;

R2 is hydrogen, halogen, unsubstituted or substituted benzyl, —C(O)—R8, $C_1$-$C_{20}$-alkyl, $C_2$-$C_{20}$-alkenylalkyl, $C_3$-$C_6$-cycloalkyl, $C_1$-$C_{20}$-alkoxyalkyl, $C_1$-$C_{20}$-hydroxyalkyl, $C_1$-$C_{20}$-alkoxy, unsubstituted or substituted aryl R3 is

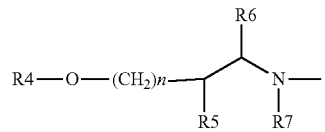

R4 is hydrogen, $C_1$-$C_{20}$-alkyl, benzyl, or —C(O)—R8;

n is 0 or 1;

R5, R6 and R7 are each independently of each other hydrogen, halogen, unsubstituted or substituted benzyl, —C(O)—R8, $C_1$-$C_{20}$-alkyl, halo-$C_1$-$C_{20}$-alkyl, $C_2$-$C_{20}$-alkenylalkyl, $C_3$-$C_6$-cycloalkyl, $C_1$-$C_{20}$-alkoxyalkyl, $C_1$-$C_{20}$-hydroxyalkyl, $C_1$-$C_{20}$-alkoxy, unsubstituted or substituted aryl; and R8 is $C_1$-$C_{20}$-alkyl, $C_1$-$C_{20}$-alkoxy, unsubstituted or substituted aryl, unsubstituted or substituted aryloxy, or benzyl.

2. The process according to claim 1, whereby the compound of formula I is a compound of the formula Ie or one of its acid addition salts

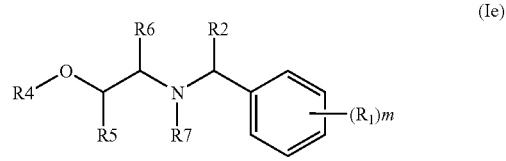

(Ie)

wherein R1, R2, R4 and m have the meanings specified for formula I in claim 1.

3. The process according to claim 2, wherein R1 is hydrogen or halogen; m is 1 or 2; R2 is hydrogen, $C_1$-$C_3$-alkyl, or phenyl; R4 is hydrogen or acetyl;

R5 is hydrogen, R6 is hydrogen or phenyl; and R7 is hydrogen; $C_1$-$C_3$-alkyl or benzyl.

4. The process according to claim 1, wherein the active ingredient employed is acetic acid 2-dibenzylamino-ethyl ester or an acid addition salt thereof.

5. The process according to claim 1, wherein the compound of formula I is applied in the form of a pour-on or spot-on formulation.

6. A process for deterring vermin from places or materials where they are not wanted, said process comprising: applying an effective amount of a compound of formula I according to claim 1 to the place or to the material, at which one would like to deter insect pests, tics or mites.

7. A composition for repelling vermin, comprising a compound of formula I

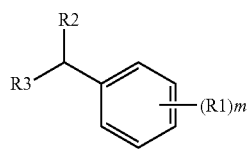

(I)

or their acid addition salts, wherein
or their acid addition salts, wherein

R1 is hydrogen halogen, $NH_2$, OH, $C_1$-$C_3$-alkyl or $C_1$-$C_3$-alkoxy;

m is 1, 2 or 3.

R2 is hydrogen halogen, unsubstituted or substituted benzyl, —C(O)—R8, $C_1$-$C_{20}$-alkyl, halo-$C_1$-$C_{20}$-alkyl, $C_2$-$C_{20}$-alkenylalkyl, $C_3$-$C_6$-cycloalkyl, $C_1$-$C_{20}$-alkoxyalkyl, $C_1$-$C_{20}$-hydroxyalkyl, $C_1$-$C_{20}$-alkoxy, unsubstituted or substituted aryl R3 is

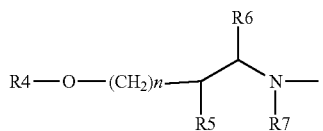

R4 is hydrogen $C_1$-$C_{20}$-alkyl, benzyl, or —C(O)—R8; wherein when R4 is H, then R2 cannot be H, and when R2 is H, R4 cannot be H;

n is 0 or 1;

R5, R6 and R7 are each independently of each other hydrogen, halogen, unsubstituted or substituted benzyl, —C(O)—R8, $C_1$-$C_{20}$-alkyl, halo-$C_1$-$C_{20}$-alyl, $C_2$-$C_{20}$-alkenylalkyl, $C_2$-$C_6$-cycloalkyl, $C_1$-$C_{20}$-alkoxyalkyl, $C_1$-$C_{20}$-hydroxyalkyl, $C_1$-$C_{20}$-alkoxy, unsubstituted or substituted aryl; and R8 is $C_1$-$C_{20}$-alkoxy, unsubstituted or substituted aryl, unsubstituted or substituted aryloxy, or benzyl;

and a spreading additive.

8. A process for the preparation of a composition for repelling vermin, whereby a compound of formula I according to claim 7 is mixed with a spreading additive.

* * * * *